US00PP08000P

United States Patent [19]

Meilland

[11] Patent Number: Plant 8,000

[45] Date of Patent: Oct. 13, 1992

[54] ROSE PLANT—MEIXERUL VARIETY

[75] Inventor: Alain A. Meilland, Antibes, France

[73] Assignee: The Conard-Pyle Company, West Grove, Pa.

[21] Appl. No.: 666,184

[22] Filed: Mar. 7, 1991

[51] Int. Cl.[5] ..... A01H 5/00

[52] U.S. Cl. ..... Plt./9

[58] Field of Search ..... Plt./7, 7.1, 9

*Primary Examiner*—Howard J. Locker

*Attorney, Agent, or Firm*—Burns, Doane, Swecker & Mathis

[57] ABSTRACT

A new and distinct variety of rose plant of the Miniature Class is provided which forms fairly abundantly attractive long lasting double blossoms. The blossoms initially are azalea pink and assume at least in part an ochre coloration when blooming is finished. The plant is bushy and forms fairly vigorous vegetation. The plant is well adapted to greenhouse forcing and also performs well when grown in the garden. Additionally, the plant is not particularly affected by cryptogamic diseases.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the Meijidiro variety (non-patented in the United States). The male parent (i.e., the pollen parent) of the new variety was the product of the pollination of the Meihigor variety (non-patented in the United States) by the Morberg variety (non-patented in the United States). The Meihigor variety sometimes is known as the Frenzy variety. The parentage of the new variety can be summarized as follows:

Meijidiro × [Meihigor × Morberg].

The seeds resulting from the above pollination were sown and 72 plantlets were obtained which were physically and biologically different from each other. Selective study resulted in the identification of a single plant of the new variety.

It was found that the new variety of Miniature rose plant of the present invention possesses the following combination of characteristics:

(a) forms in fair abundance attractive double long lasting blossoms which initially are azalea pink and turn at least in part to ochre when blooming is finished,
(b) forms fairly vigorous vegetation,
(c) exhibits a bushy growth habit,
(d) is well adapted to greenhouse forcing and also performs well in the garden, and
(e) is not particularly affected by cryptogamic diseases.

The new variety well meets the needs of the horticultural industry for all usages. It is particularly well-suited for use as attractive ornamentation as a flowering pot plant for use indoors or outdoors.

The new variety has been found to undergo asexual propagation by a number of routes, including budding, grafting, cuttage, etc. A sexual propagation by the above mentioned methods as performed in France has shown that the characteristics of the new variety are strictly transmissible from one generation to another.

The new variety has been named the Meixerul variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were one year of age and were observed during February while growing on their own roots in greenhouses at Le Cannet des Maures, Var, France.

DETAILED DESCRIPTION

Figures 1, 2, 3, 4, 5, 6, 7, 8, 9, 10, 11, 12, 13, 14, 15, 16, 17:
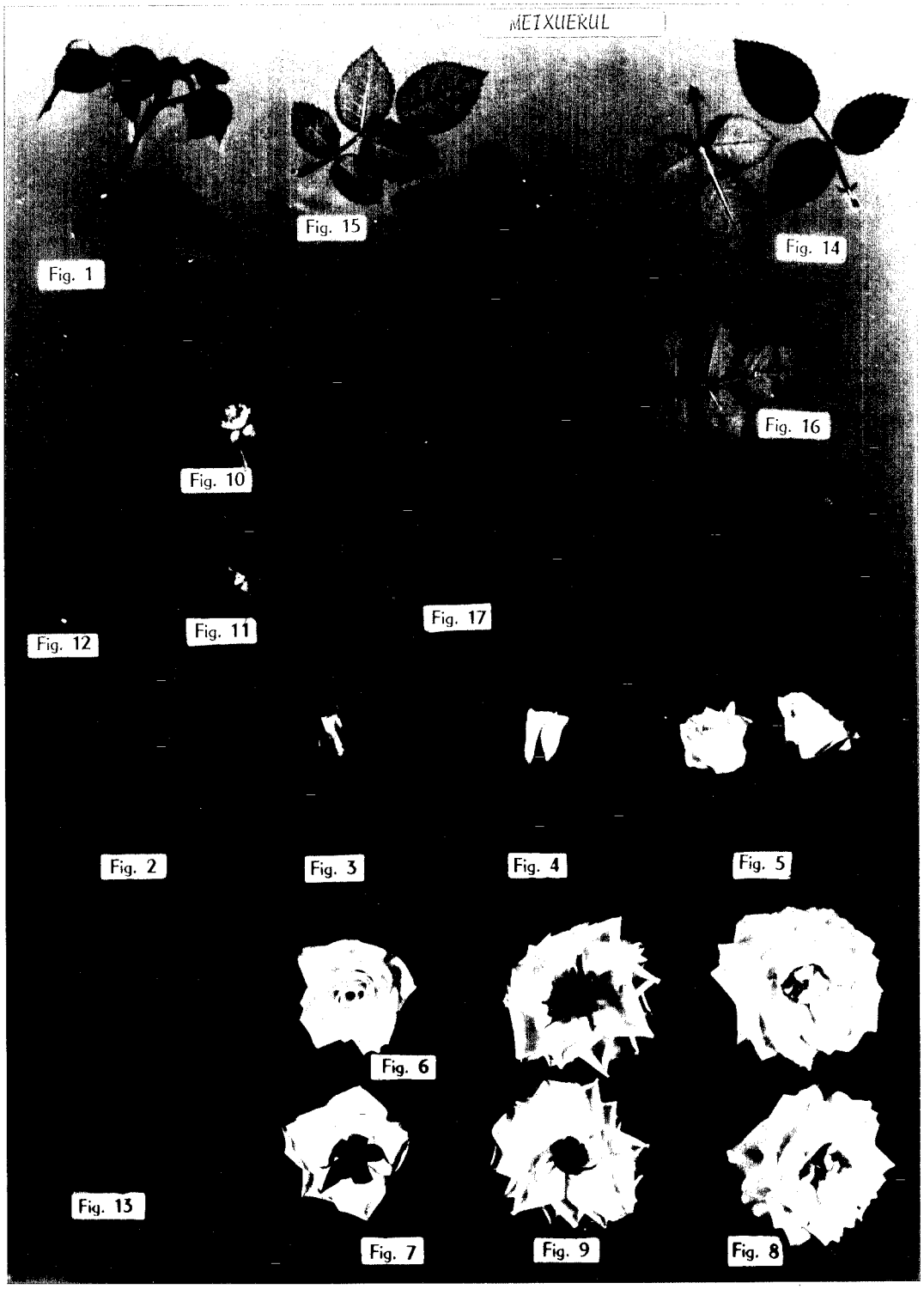
FIG. 1 illustrates a specimen of a young shoot.
FIG. 2 illustrates specimens of two floral buds before the opening of the sepals.
FIG. 3 illustrates a specimen of a floral bud at the opening of the sepals.
FIG. 4 illustrates a specimen of a floral bud at the opening of the petals.
FIG. 5 illustrates specimens of two flowers in the course of opening.
FIG. 6 illustrates a specimen of a flower in the course of opening — plan view — obverse.
FIG. 7 illustrates a specimen of a flower in the course of opening — plan view — reverse.
FIG. 8 illustrates specimens of two fully open flowers — plan view — obverse.
FIG. 9 illustrates specimens of two fully open flowers — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets with the upper surface being shown at the upper right and the under surface being shown at the lower left.
FIG. 15 illustrates specimens of leaves with five leaflets with the under surface being shown on the top and the upper surface being shown on the bottom.
FIG. 16 illustrates specimens of leaves with seven leaflets with the under surface being shown on the top and the upper surface being shown on the bottom.
FIG. 17 illustrates a specimen of a leaf with nine leaflets showing the upper surface.

The chart used in the identification of the colors is that of The Royal Horticultural Society (R.H.S. Colour Chart). The terminology which precedes reference to the chart has been added to indicate the corresponding colors in common terms. The description is based on one year old specimens of the new variety which were observed during February while growing on their own roots in greenhouses at Le Cannet des Maures, Var, France.

Class: Miniature.

Plant:

*Height.*—Approximately 18 to 20 cm. on average.

*Habit.*—Bushy.

Branches:

*Color.*—Young stems: lettuce green, Green Group 143C. Adult wood: medium green, Green Group 143A.

*Thorns.*—Size: very narrow. Quantity: few. Color: pinkish on young stems and greenish changing to light tan on adult wood.

Leaves:

*Petioles.*—Upper surface: striped, light green on young foliage and medium green on adult foliage with more or less glandular edges. Under surface: light green with a few prickles.

*Stipules.*—Adnate, pectinate, narrow and linear.

*Leaflets.*—Number: 3, 5, 7 (most often), and 9. Shape: oval. Serration: single and regular. Texture: consistent. General appearance: fairly dense and semi-dull. Color (young foliage): Upper surface: lettuce green, Yellow-Green Group 144A. Under surface: lettuce green, Yellow-Green Group 144A. Color (adult foliage): Upper surface: medium green, Green Group 137B. Under surface: light green, Green Group 137D.

Inflorescence:

*Number of flowers.*—Approximately 1 to 2 and very seldom 3 per stem.

*Peduncle.*—Straight, light green and more or less stained with reddish coloration, more or less covered with glandular aciculae, and its length is approximately 3 cm. on average.

*Sepals.*—Upper surface: tomentose and greenish in coloration. Under surface: light green, more or less stained with reddish coloration, and the outer sepals may or may not be slightly appendiculated.

*Buds.*—Shape: conical. Length: approximately 1.5 cm. on average. Size: small. Color upon opening: Upper surface: light pink, Red Group 37B. Under surface: light pink, Red Group 37C, and edged with Red Group 37B.

*Flower.*—Form: cuplike, and fully double. Diameter: approximately 5 to 5.5 cm. on average. Color (when opening begins): Upper surface: azalea pink, Red Group 38A. Under surface: light azalea pink, Red Group 38C, suffused with azalea pink, Red Group 38A. Color (when blooming): Upper surface: azalea pink, Red Group 38B, more or less suffused with azalea pink, Red Group 38A. Under surface: light azalea pink, Red Group 38C, more or less suffused with azalea pink, Red Group 38A. Color (at end of blooming): Upper surface: Jasper red, Red Group 39C, and widely stained with orange buff, Yellow-Orange Group 22D, at the base of the petals. Under surface: Jasper red, Red Group 39C, and more or less tinted with orange buff, Yellow-Orange Group 22D, at the base of the petals. Fragrance: slight. Lasting quality: long. Petal number: approximately 30 to 34 on average. Petal form: the outer petals are rounded with a well-pronounced tip, and the inner petals are oval. Petal texture: consistent. Petal drop: good. Anthers: normal and yellowish in coloration. Stamen number: approximately 56 to 60 on average. Filaments: well planted around the receptacle, greenish in coloration, and of irregular heights. Pistil number: approximately 35 to 40 on average. Stigmas: normal and straw-like in coloration. Styles: light fuschia in coloration, and of irregular heights. Receptacle: medium green, and in longitudinal section is in the shape of a pitcher.

Development:

*Vegetation.*—Fairly vigorous.

*Blooming.*—Fairly abundant.

*Aptitude to bear fruit.*—Good.

*Resistance to diseases.*—Good.

I claim:

1. A new and distinct variety of Miniature rose plant characterized by the following combination of characteristics:

(a) forms in fair abundance attractive double long lasting blossoms which initially are azalea pink and turn at least in part to ochre when blooming is finished,
(b) forms fairly vigorous vegetation,
(c) exhibits a bushy growth habit,
(d) is well adapted to greenhouse forcing and also performs well in the garden, and
(e) is not particularly affected by cryptogamic diseases;

substantially as herein shown and described.

* * * * *

MEIXUERUL